(12) United States Patent
Strommer

(10) Patent No.: US 7,209,543 B2
(45) Date of Patent: Apr. 24, 2007

(54) AUTOMATIC EXPOSURE METHOD AND AUTOMATIC EXPOSURE SYSTEM

(75) Inventor: Pekka Strommer, Espoo (FI)

(73) Assignee: Planmed Oy, Helsinki (FI)

( * ) Notice: Subject to any disclaimer, the term of this patent is extended or adjusted under 35 U.S.C. 154(b) by 141 days.

(21) Appl. No.: 10/496,329

(22) PCT Filed: Nov. 25, 2002

(86) PCT No.: PCT/FI02/00948

§ 371 (c)(1),
(2), (4) Date: Oct. 27, 2004

(87) PCT Pub. No.: WO03/043497

PCT Pub. Date: May 30, 2003

(65) Prior Publication Data

US 2005/0078792 A1 Apr. 14, 2005

(30) Foreign Application Priority Data

Nov. 23, 2001 (FI) .................................. 20012307

(51) Int. Cl.
*H05G 1/42* (2006.01)
(52) U.S. Cl. ...................................... 378/97; 378/108
(58) Field of Classification Search ............... 378/37, 378/97, 108
See application file for complete search history.

(56) References Cited

U.S. PATENT DOCUMENTS

| 4,090,084 A | 5/1978 | Epstein et al. | |
| 4,455,669 A | 6/1984 | Aichinger et al. | |
| 4,763,343 A | 8/1988 | Yanaki | |
| 5,218,625 A | 6/1993 | Heidsieck | |
| 5,347,563 A * | 9/1994 | Heidsieck ................. | 378/62 |
| 6,151,383 A * | 11/2000 | Xue et al. ................. | 378/108 |
| 6,192,105 B1 * | 2/2001 | Hunter et al. ............. | 378/108 |
| 6,459,765 B1 * | 10/2002 | Ganin et al. .............. | 378/108 |
| 6,502,984 B2 * | 1/2003 | Ogura et al. ............. | 378/206 |
| 6,553,095 B2 * | 4/2003 | Rinaldi et al. ............ | 378/108 |
| 6,754,307 B2 * | 6/2004 | Brendler et al. ........... | 378/108 |
| 2002/0085672 A1 | 7/2002 | Ganin et al. | |

FOREIGN PATENT DOCUMENTS

| EP | 0 346 530 A1 | 12/1989 |
| EP | 1 004 875 A2 | 5/2000 |
| WO | WO 00/52641 | 9/2000 |

* cited by examiner

*Primary Examiner*—Edward J. Glick
*Assistant Examiner*—Thomas R. Artman
(74) *Attorney, Agent, or Firm*—Wolf Block Schorr & Solis-Cohen LLP

(57) ABSTRACT

The present invention relates to automatic exposure control implemented in imaging by electromagnetic radiation, in particular to automatic exposure control in film-based mammography, which is based on a completely new approach as compared with the solutions currently in use, which utilize adjustment curves and/or tables constructed on the basis of empiric tests. The new approach includes modeling into the AEC system the radiation spectra obtainable from the radiation source as a function of its operating parameters and attenuation of the spectrum as the radiation traverses components of the imaging apparatus. By measuring the thickness of the object to be imaged and knowing the initial spectrum and its calculable behavior, a correspondence between the AEC signal and the desired darkening of the image can be achieved which is based on true density of the object being imaged.

27 Claims, 3 Drawing Sheets

AUTOMATIC EXPOSURE METHOD AND AUTOMATIC EXPOSURE SYSTEM

FIELD OF INVENTION

The present invention relates to automatic exposure implemented in imaging by electromagnetic radiation, in particular to automatic exposure in film-based mammography.

BACKGROUND OF THE INVENTION

In prior art, numerous different automatic exposure control (AEC) systems are known, which have been applied in connection with many different imaging solutions. In diagnostic X-ray imaging, exposure automation plays a very important role because its incorrect operation may lead to over- or underexposure and consequently to an unnecessary increase in the radiation dose received by the patient and to uncertain or even wrong diagnoses due to bad image quality. Incorrect exposures can of course be remedied via repeated imaging, but this further increases the radiation dose received by the patient and, on the other hand, it also involves extra work and expenses.

As the development of the film/intensifying screen combinations used in mammographic apparatus is making them increasingly sensitive and steep, automatic exposure solutions that have worked well to date may prove to be insufficient and they can not necessarily keep darkening of the film within acceptable limits, especially when operation of the automatic exposure system is being tested by varying the imaging parameters and object to the extent required by authority regulations.

The operation of automatic exposure systems currently in use is based on an empiric method in which each new film/intensifying screen combination is subjected to an enormous number of exposure tests using different imaging values of the imaging apparatus and varying the thickness, generally in range of 20–80 mm, of the acrylic plate typically used to represent the object to be imaged. Depending on the details of operation of the automatic exposure system used in each case, its various parameters are adjusted according to the results obtained until a sufficiently constant degree of film darkening is achieved in all circumstances. Each time when a new film/intensifying screen combination appears on the market or when more demanding tolerance requirements are set, such measurement series have to be carried out anew.

The commonly used calibration method as described above is thus based on radiographing a homogeneous plate, generally made of acrylic, simulating the object to be imaged. The periodic inspections carried out by the authorities to test the exposure automatics are based on the same method, which, it is true, is even necessary in respect of repeatability of the test. However, in an actual imaging situation, the object being imaged is not necessarily homogeneous. For example, the breast tissue imaged in mammography is by no means homogeneous, nor is the breast of standard size or shape in overall dimensions. As the object is typically also imaged from different projections in mammography, its shape and position in the imaging area may vary for this reason, too.

Already in early automatic exposure systems of mammographic apparatus, to allow for variation in the properties of the objects, the detector part of the automatic exposure system was movably arranged and the operator of the apparatus was expected to have the skill to select the optimal position for the detector for the measurement. Alternatively, the apparatus could have several detectors, of which the operator could choose the most suitable one. However, manual positioning of the detector involves certain problems and it may be incorrectly placed, e.g. partially outside the tissue to be imaged, with the result that radiation hitting the detector directly will stop the exposure too early. On the other hand, for example if the tissue being imaged contains a local dense part that happens to lie precisely in front of the detector, the exposure time may become too long. Therefore, especially in screening imaging where the imaging tempo is very rapid, incorrect detector positioning easily leads to errors regarding the degree of film darkening and thus may even create a need for repeated imaging as described above.

To eliminate the above-described problems regarding positioning of the detector, solutions using multiple detectors have been developed in which the signal produced by those detectors which have received quantity of radiation exceeding a given preset level is automatically left out of account. This limit level is so defined that, in order to reach it, the detector must obviously be located completely or partly outside the tissue being imaged. Solutions have also been developed in which a few detectors are used, of which the one is selected whose output signal appears to be the most suitable. While these solutions have significantly reduced exposure errors, they still involve the problem that their operation is only based on empirical knowledge that has proven to be good, and extending or adjusting such a function according to new and/or more demanding requirements may be very difficult and laborious, even impossible. In view of the latest proposals put forward by the authorities, in the future such requirements may include e.g. that the average film darkness should be determined with an accuracy of −+0.15 OD (Optical Density) (the figure is constant, but varies between 1.2 OD and 1.8 OD according to new research results and weightings varying from one country to another), but in the lightest areas of the film a certain minimum darkening should be guaranteed to ensure that a tumor, which is often located in exactly these dense areas of the tissue, can be diagnosed.

OBJECTS AND SUMMARY OF THE INVENTION

In summary, the basic idea of automatic exposure control is to measure the signal produced in the AEC detector by the radiation used for imaging and, based on this measurement, to estimate the exposure received by the film. In prior art this relation, which is influenced e.g. by the voltage of the radiation source used in imaging, filtering of radiation emitted from the radiation source and the thickness and density of the tissue being imaged, has been found by empiric means—and by using for finding out these correlations only one object density, such as that of an acrylic plate. Actual adjustment of the imaging parameters of the radiation source during imaging is performed according to adjustment curves and/or tables constructed on the basis of these measurement results. In the case of mammographic apparatus, in practice this means performing thousands of imaging tests by taking into account dozens of different variables, documenting the results obtained from these imaging tests and constructing correlation tables/curves as described above from this data.

The object of the present invention is to achieve a solution for implementing automatic exposure control that is based on a completely new approach as compared with the solutions currently used and thus to enable an automatic exposure control system that, as compared with earlier systems, is more accurate and more adaptable to the anatomy of the object to be imaged, the operation of the system being based on a knowledge and modeling of the spectrum of the actual radiation used for imaging, and of the changes of the spectrum.

On the other hand, according to one of the special objects of the invention, the aim is to determine any local deviations of the tissue type being imaged from the average so that the imaging parameters can be adjusted to optimal values for the object in question.

In precise terms, the aims of the invention are achieved by the solutions defined in the claims below. A preferred embodiment of the invention for controlling exposure in film-based mammographic imaging is thus based on an approach completely different from the methods known at present, in which approach, on the basis of the imaging parameters used and modelings as taught by the invention, the radiation spectrum emitted by the radiation source is already known when imaging is started, as is the behavior of this spectrum on the path of radiation towards the object to be imaged and further towards the exposure detector and the device receiving the imaging information. The changes occurring in the radiation spectrum as it passes through different material layers can be calculated using the known equation describing the attenuation of monochromatic radiation:

$$I = I_0 \times e^{-1\mu}$$

where I=intensity of radiation leaving the object, $I_0$=intensity of radiation incident on the object, 1=distance traversed by the radiation in the object and µ=linear attenuation coefficient depending on the atomic composition of the object and energy of the radiation quantum.

More precisely speaking, the invention is thus based on a principle in which the initial data known at the start includes e.g. the kV of the radiation source as well as the anode material and anode angle of the X-ray tube used for imaging, so the spectrum of the radiation beam can be determined very accurately by means known in themselves (see e.g. Phys.Med.Biol. Vol. 24, 505 (1997)). On the other hand, as the materials and material thickness of those components of the imaging apparatus that lie between the radiation source and the object during imaging are also known beforehand, the spectrum of the radiation penetrating into the tissue to be imaged can further be accurately determined computationally. Further according to the invention, as the thickness of the object to be imaged in its imaging position is determined before the imaging is started, it is also possible to calculate in advance what the spectrum of the radiation having passed through the object would be like if the composition of the object, or in fact its density relative to the radiation used for the imaging, were typical of the object and of an "average level". As the structure and operating principle of the AEC detector as well as the materials and material thickness of the components of the imaging apparatus lying between the object and the AEC detector are also precisely known beforehand, it is further possible to calculate what kind of signal would be obtained in this case from the exposure detector and, on the other hand, also the degree of darkening of the image produced that this would correspond to. Now, if after beginning of the imaging the AEC signal is found to be different from the assumed one, then this will be known to be due to the density of the object—relative to the radiation used—differing from what it was assumed to be. On the basis of the AEC signal and the object thickness data it is then possible to computationally determine what object density the measured AEC signal corresponds to and thus further to calculate the effect of the object, whose density is now known, on the spectrum, in other words, to calculate the spectrum behind the object. Thus, it is further possible to accurately determine, among other things, the number of light photons absorbed by the film per signal unit measured by the exposure detector and thus, to adjust the imaging parameters to optimal values.

BRIEF DESCRIPTION OF THE DRAWINGS

In the following, the invention will be described in detail as applied to implementation of automatic exposure control in a typical film-based mammographic apparatus and by referring to the attached drawings, wherein.

DETAILED DESCRIPTION OF THE INVENTION

Figure 1:
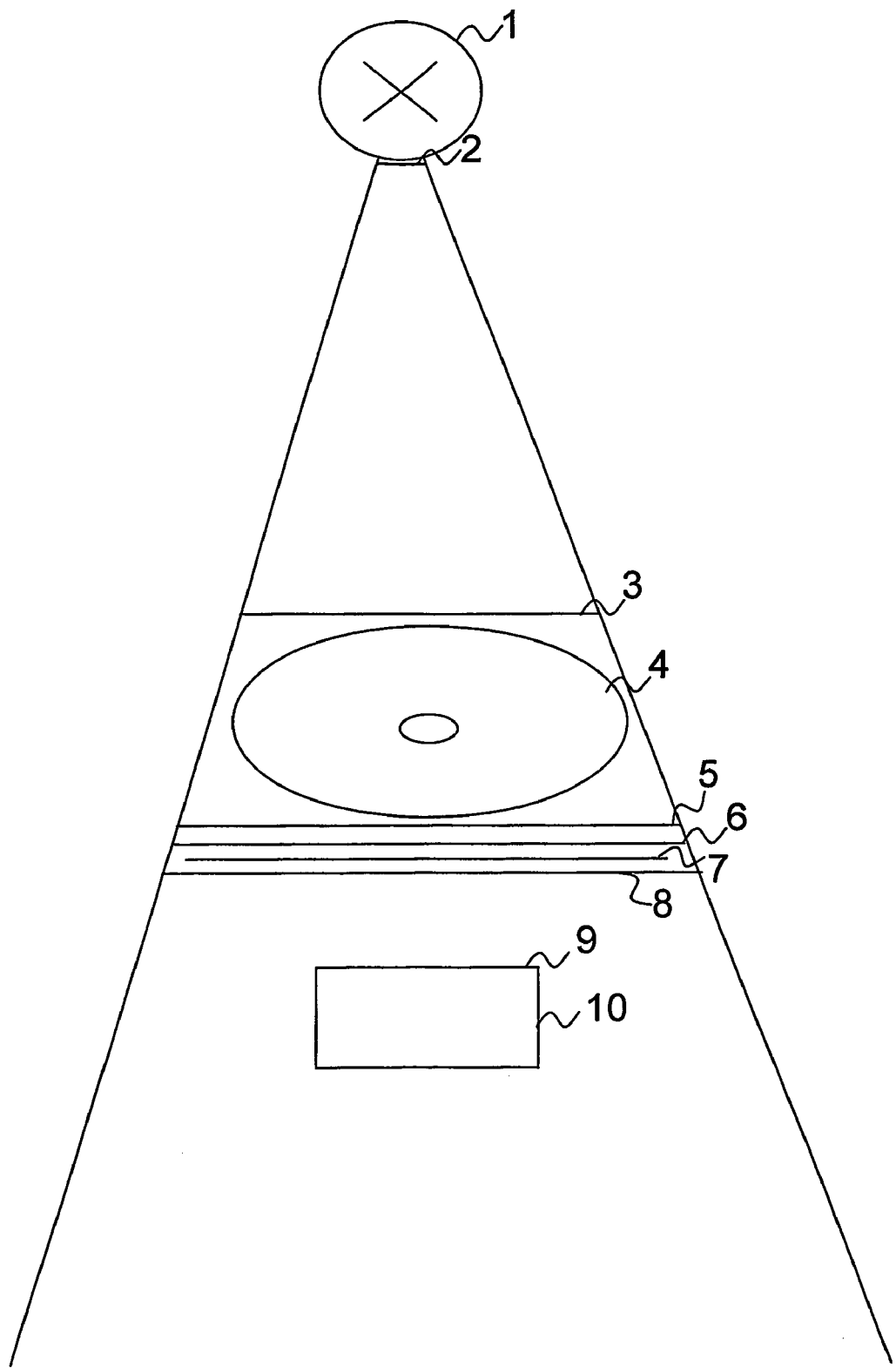
FIG. 1 presents cross-sectional view of the structures of a typical mammographic apparatus that lie in the area of the beam during imaging.

FIG. 1 presents a cross-sectional view of those structures of a typical mammographic apparatus that are penetrated during imaging by an X-ray beam produced by an X-ray tube (1). As shown in FIG. 1, these structures include a filter (2), an upper compression plate (3) compressing the breast in the imaging area, a breast (4), a lower compression plate (5), a film cassette cover (6), a film (7), a film cassette bottom with an intensifying screen (8) and a cover (9) of an AEC detector. Information regarding the materials of all these components and their thickness in the direction of the beam can be stored in the memory of the imaging apparatus or a computer connectable to it, along with information needed in the calculation processes comprised in the automatic exposure system of the invention, i.e. information about different filters to be used in the apparatus, the films and their intensifying screens used in different film cassettes, the epitaxial layer thickness of the exposure detector, etc. According to the invention, the only item of information to be stored in memory that is necessarily based on empiric tests is a table of the quantity of radiation produced by the X-ray tube at some of its operating parameters, all the rest can be calculated.

Figure 2A:
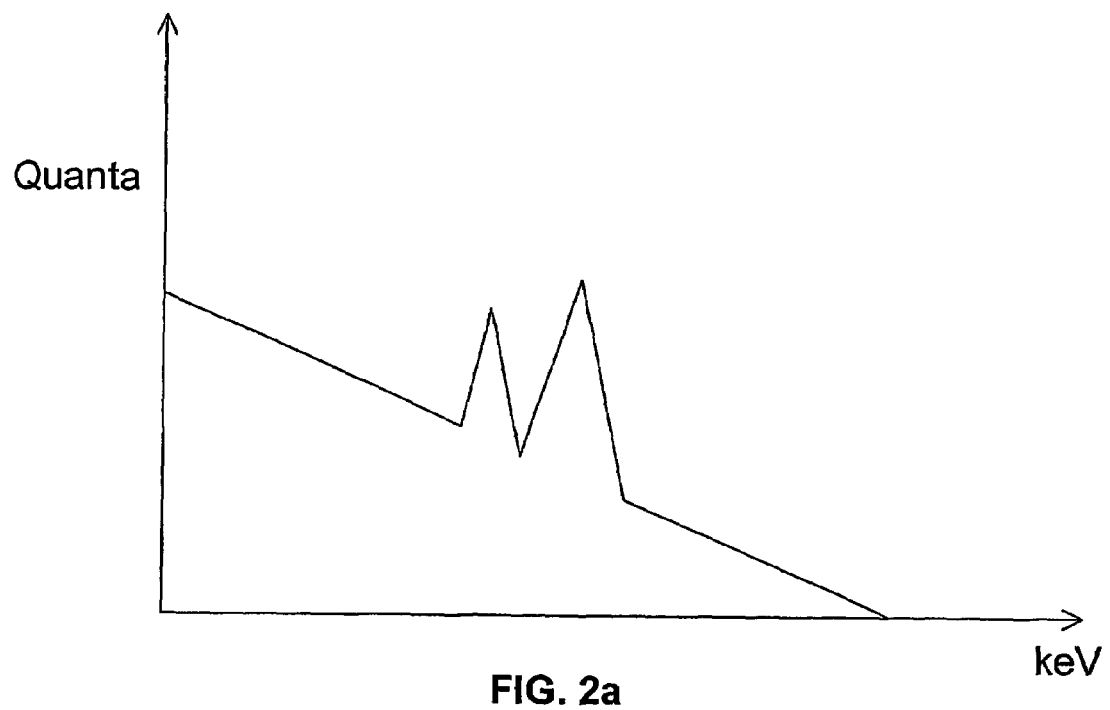
FIGS. 2*a* and 2*b* present typical spectra of radiation obtained from an X-ray tube before and after filtering.
Figure 2B:
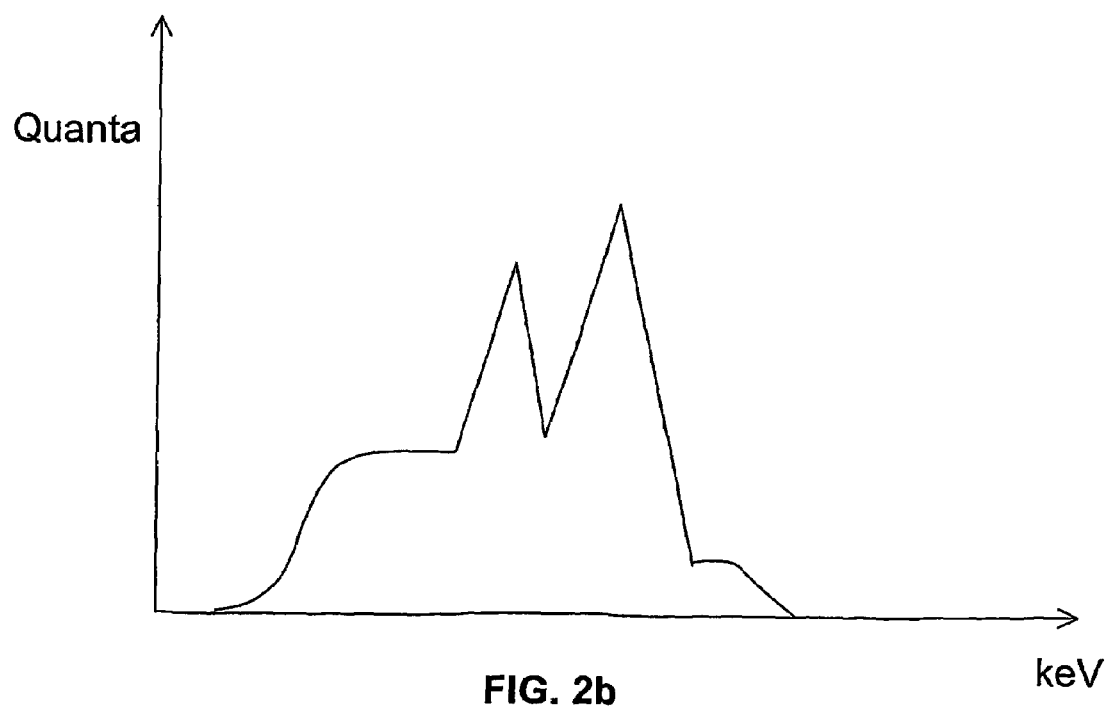

At the start of the imaging process, e.g. the kV and mA to be used for imaging are first input to the X-ray apparatus, or alternatively the control system of the apparatus can automatically select the values it assumes to be optimal according to the distance between the compression plates after the breast has been compressed between them to its imaging position. On the basis of the information stored in memory, the radiation spectrum emitted by the X-ray tube is known exactly already at this point, i.e. before the exposure is started. Further, as the material used for filtering the radiation obtained from the X-ray tube and its thickness are also known, as well as corresponding data about the compression plate, the radiation spectrum penetrating into the breast being imaged can be accurately determined computationally. FIGS. 2*a* and 2*b* show an example of how the spectrum (FIG. 2*a*) obtained with certain X-ray tube operation parameters and filter materials may change after passing through a filter (FIG. 2*b*).

When the compression thickness of the breast being imaged is known, it is possible even before the exposure is started to computationally establish what the radiation spectrum having penetrated it would be like with the imaging parameters used, if the tissue was of average nature, and thus further to determine what the radiation spectrum falling on the AEC detector (10) used in the apparatus would be like, in this case as in the embodiment as illustrated in FIG. 1, after the radiation has further passed through the lower compression plate (5), the film cassette and its intensifying screen (6, 7, 8) and the cover (9) of the AEC detector. (In principle, the AEC detector might also be placed somewhere else than behind the cassette—however, in mammography it could be said being non-allowable even to place the detector such that it could interfere with the image of the actual object to be imaged). Thus, on the basis of this computed spectrum, and the thickness of the epitaxial layer of the diode typically used as AEC detector, it is also possible to calculate by known means what the electric signal generated in the detector should be.

The actual AEC function is started immediately after the beginning of imaging. On the basis of the signal obtained from the AEC detector and the known imaging parameters and tissue thickness data, the tissue density that the measured AEC signal corresponds to can now be determined, whereupon it is further possible to calculate the effect of the tissue, whose density is now known, on the radiation spectrum having penetrated the tissue. Thus, it is possible, as described in some more detail below, to determine the exact number of light photons absorbed by on the film per each signal unit measured by the exposure detector and to adjust the imaging parameters, especially the exposure time, to optimal values.

The adjustment of darkening of the film used for imaging is now described in some more detail. As a result of the above-described determinations and modelings performed before exposure, it is possible to determine the quantity and spectrum of the radiation absorbed into the film inside the film cassette on the one hand and into the intensifying screen (8) on the other in the case of "average" tissue (4). On the basis of the known properties of the intensifying screen (8)—which is a layer of a material at the bottom of the X-ray cassette that absorbs X-ray quanta and emits them further as converted into light photons—it is further possible to calculate the number of light photons generated, which is directly proportional to darkening of the film (7). Thus, in principle, the required exposure time for tissue having an assumed density is already known at this stage, and it would of course be also possible to perform the imaging by executing the exposure straightforwardly on the basis of this information, and use corrected imaging parameters only if the AEC signal significantly differs from the calculated signal. In mammography, it would be further possible to integrate with such a function a correction factor based on the object thickness data, such that for a thickness smaller than average the object being imaged would be estimated to have a density greater than average and vice versa, in other words, that for small thickness values the exposure time would be slightly increased in relation to the exposure time obtained from the above-mentioned determination and vice versa. However, density of breast tissue varies so much that in practice it would generally not be possible to reach desired darkening with sufficient accuracy by such means only. According to the invention, however, as the density of the tissue being imaged and thus the radiation spectrum having penetrated the object can be calculated on the basis of the measurement performed during the imaging, it is further possible to calculate the number of the X-ray quanta absorbed directly into the film and to determine the radiation spectrum absorbed into the intensifying screen of the film cassette and subsequently the number of light photons produced by it, and thus further the required exposure time.

Without departing from the basic concept of the invention, many other items of information based on or calculated from empirical tests as well as other pieces of information and calculation models can be stored in memory to allow them to be utilized in the automatic exposure system. Such information may include e.g. control algorithms known in themselves for the adjustment of other imaging parameters besides exposure time—to be utilized e.g. when the imaging parameter values assumed to be optimal in the starting situation turn out, on the basis of the measured AEC signal, to be significantly different from the values that would allow an optimal imaging result to be achieved as a function of e.g. exposure time, kV, mA, focus size of the X-ray tube etc. used, and possible different combinations of these. On the other hand, the above-described film-based AEC function can be further improved by implementing it in a manner such that it takes into account the feature characteristic of films that they do not behave according to the reciprocal law. In this case, the exposure time leading to correct film darkening for the film type used, and a correction factor dependent on it, which corrects the exposure time to be the longer the longer is the exposure time, are also modeled into the system. The values needed for calculation of the optimal exposure time that takes this deviation into account are typically supplied by the manufacturer of the film. In practice it is further advisable to include in the system a model of the effect of the radiation scattered from the object on the AEC detector signal as a function of object thickness, and perhaps also a model of the effect of the radiation scattered from the components of the apparatus itself.

Figure 3:
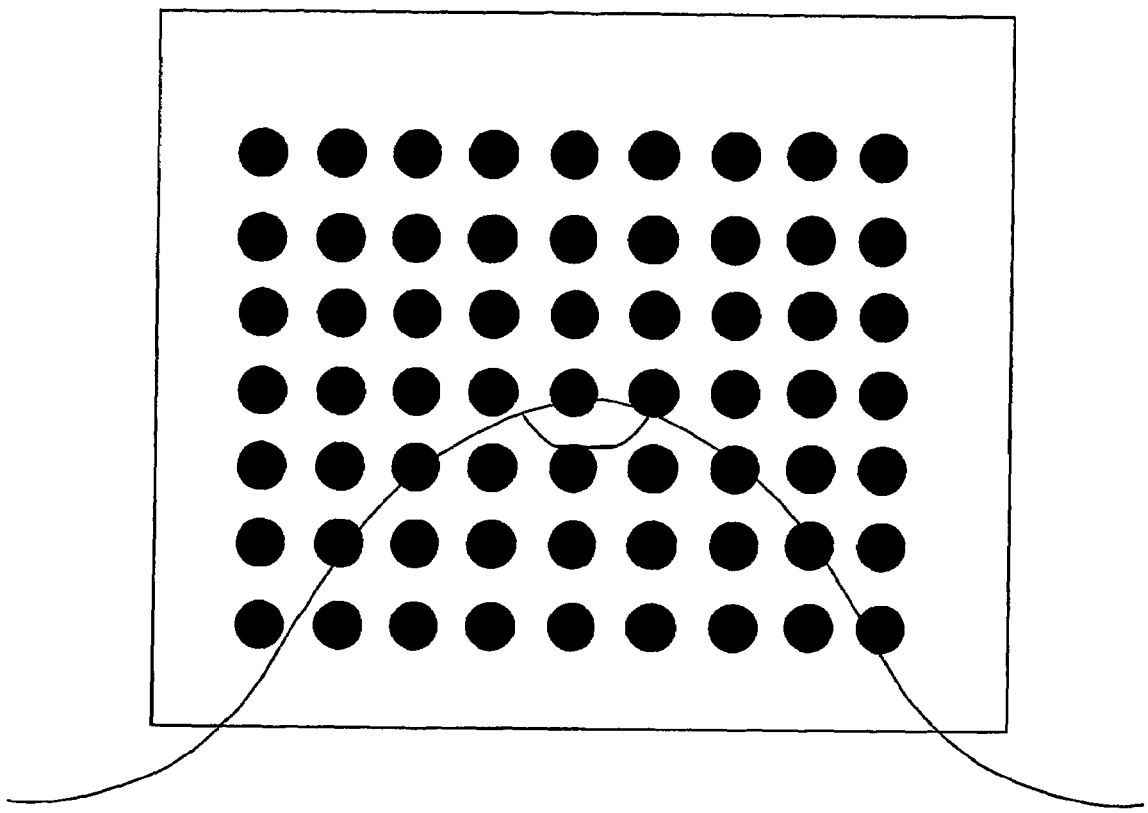
FIG. 3 presents an exposure detector structure advantageous for implementing the invention, consisting of a plurality of small detectors.

According to the invention, it is additionally advantageous to measure the object from as many points as possible, from small local areas. In this way it is possible to avoid the problems described earlier which may result if only one exposure detector is used, in case it happens to lie behind a non-representative part of the tissue or even partly or completely outside the object. With modern technology, it is not really a matter of cost to provide the AEC detector (10) with even dozens of small detectors (10', 10'', . . . ) arranged apart from each other in the object area e.g. as shown in FIG. 3. As an advantage of this solution, a representative view is obtained as to what proportion of the tissue (4) is of average density and/or deviating from it in either direction. Based on this information, the imaging parameters can then be adjusted so that areas of greater density will not be too light in the image produced and areas of lesser density will not be too dark to be readable. On the other hand, with such a solution it is possible to accomplish at least a satisfactory control of a situation where the object contains areas of such widely varying densities that there is no possibility to achieve a result that is optimal in all respects, in other words, where the required dynamic range would be too broad. In such a case, the imaging parameters can be optimized so as to enable a result to be achieved in which a maximal portion of the tissue being imaged is still readable from the image.

On the basis of modeling according to the invention, it is easy even in an application of the above-described type to distinguish those detectors which obviously lie completely or partly outside the breast tissue being imaged, because the measurement result they produce is much too high, in other words, because the breast typically does not contain tissue having such a low density. Likewise, on the basis of suitable criteria built into the system, detectors lying very close to the edge of the tissue being imaged can be identified and the signal given by them corrected. Since the signal produced by detectors lying completely outside the object does not represent the properties of the tissue, it is hardly sensible to use them for the adjustment of imaging parameters except for a minor proportion for the most. However, if desirable, the signal provided by such detectors can be used for measuring radiation output of the apparatus and thus for compensating possible variations in it.

In the foregoing, the invention has been described in the first place as applied to a film-based mammographic apparatus, but naturally it can also be used in connection with other imaging applications and image data receiving means and e.g. using any known AEC detector technology. The invention and its embodiments are therefore not limited to the solutions described above; instead, they may be varied within the scope of the following claims.

What is claimed is:

1. Automatic exposure method for use in a diagnostic imaging apparatus in which an object to be imaged is positioned in an imaging area, a radiation source is used to produce radiation for use in the imaging process, radiation containing image information is detected by an image data receiving means and at least one imaging parameter is controlled during exposure on the basis of a signal detected by an at least one exposure detector, wherein the method comprises at least the following actions:

modeling the radiation spectrum obtained from the radiation source of the imaging apparatus as a function of said at least one operating parameters and production of radiation quanta, in a case where the imaging apparatus has components that lie between the radiation source and the image data receiving means, modeling in respect of attenuation of radiation at least one of said components of the imaging apparatus that lie between the radiation source and the image data receiving means, and in a case where the imaging apparatus has components that lie between the radiation source and the exposure detector, modeling at least one of said components that lie between the radiation source and the exposure detector with respect to attenuation of radiation;

modeling darkening of the image being detected by the image data receiving means as a function of radiation incident on the image data receiving means, determining thickness of the object to be imaged within the imaging area in the direction of a radiation beam emitted from said radiation source, beginning the exposure, measuring a signal obtained from an exposure detector and determining the object density by comparing the signal to the modeled attenuation of radiation, and on the basis of the aforesaid modelings, the determined object thickness, and the determined object density, determining at least one value of the at least one imaging parameter required to achieve a desired degree of darkening of the image and adjusting the at least one imaging parameter accordingly.

2. Automatic exposure method according to claim 1, wherein each modeled component is modeled using an equation of coherent monochromatic radiation on the basis of a material composition and a thickness of each modeled component.

3. Automatic exposure method according to claim 1, wherein for at least one of the aforesaid components of the imaging apparatus, correlation between different radiation intensities and attenuation of the radiation spectrum caused by said component is determined via empiric measurements.

4. Automatic exposure method according to claim 1, wherein the image data receiving means is a photographic film, and further wherein said step of modeling darkening of the image being detected by the image data receiving means is modeled by taking into account the radiation quanta absorbed directly into the film since having penetrated through a cover of a film cassette and the radiation quanta converted into light photons in an intensifying screen and emitted from there to the film, on the basis of a spectrum calculated from said step of modeling the radiation spectrum and said step of modeling in respect of attenuation of radiation at least one of the components of the imaging apparatus that lie between the radiation source and the film, wherein the at least one component includes the cover of the film cassette.

5. Automatic exposure method according to claim 4, wherein the signal obtained from the exposure detector considering the radiation spectrum used for the imaging, the thickness of the object and the attenuation of the radiation according to the aforesaid modelings, is determined assuming that the attenuation in the object is typical of the object and of average magnitude, an exposure time according to said modelings and corresponding to said signal is determined, exposure is begun, the exposure detector signal is measured and compared to the exposure detector signal determined on the basis of the modelings and, if the measured signal differs from the predetermined signal by more than a preset limit criterion, the exposure time and/or some other imaging parameter is adjusted to a value corresponding to the actual object density determined on the basis of said modelings.

6. Automatic exposure method according to claim 1, wherein the radiation containing image data is detected using a film whose darkening deviating from the reciprocal law is known and the at least one imaging parameter is corrected correspondingly, where the at least one imaging parameter is an exposure time.

7. Automatic exposure method according to claim 6, wherein the exposure time is corrected taking into account an exposure time determined from said modelings which leads to desired darkening and is consistent with a correction factor representing deviation from the film type used.

8. Automatic exposure method according to claim 1, wherein the imaging apparatus is a mammography imaging apparatus, wherein the mammography imaging apparatus has at least one component that lies between the radiation source and the image data receiving means and/or between the radiation source and the exposure detector, and wherein said at least one component includes at least one of the following: a radiation filter, compression plates, a film cassette cover, a film, an intensifying screen, a film cassette bottom and an exposure detector cover.

9. Automatic exposure method according to claim 1, wherein all components lying between the radiation source and the image data receiving means are modeled as a function of attenuation of radiation.

10. Automatic exposure method according to claim 1, wherein all components that lie between the radiation source and the exposure detector are modeled as a function of attenuation of radiation.

11. Automatic exposure method according to claim 1, wherein a plurality of exposure detectors are used.

12. Automatic exposure method according to claim 11, wherein the signal of each detector is measured, and these signals are weighted so that no part of the image produced will remain too light nor darken too much.

13. Automatic exposure method according to claim 11, wherein said step of determining the at least one value of the at least one imaging parameter is a step of determining a value corresponding to an exposure time, and further wherein said step of determining the at least one value includes the step of evaluating said signals measured from the plurality of exposure detectors on the basis of the magnitude of the measured signal and the density of the object, in order to determine whether the corresponding exposure detector lies within the area under the object or outside the area under the object, and further wherein any of said signals corresponding to an exposure detector that lies outside the area under the object are not taken into consideration when determining said value corresponding to the exposure time.

14. Automatic exposure method according to claim 13, wherein the method additionally comprises the steps of determining a variation in the production of radiation quanta and providing compensation to compensate for said variation, wherein said step of determining a variation is based upon at least one of the signals measured from the plurality of exposure detectors that corresponds to an exposure detectors lying outside the area under the object.

15. Automatic exposure system for use in a diagnostic imaging apparatus, said imaging apparatus comprising means for positioning an object (4) to be imaged (3, 5) in an imaging area, a radiation source (1) producing radiation for use in the imaging process, means for detecting radiation containing image information (7), means for generating a control signal (10) and for controlling at least one imaging parameter on the basis of said control signal during imaging, wherein the automatic exposure system comprises data storage means containing modelings of the radiation spectrum obtained from the radiation source (1) of the imaging apparatus as a function of said at least one imaging parameter and production of radiation quanta, in a case where the imaging apparatus has components that lie between the radiation source (7) and the image data receiving means (7), at least one of the components (2, 3, 5,) of the imaging apparatus that lie between the radiation source (1) of the imaging apparatus and the image data receiving means (7), and in a case where the imaging apparatus has components that lie between the radiation source and the exposure detector, at least one of the components (2, 3, 5, 6, 7, 8, 9) that lie between the radiation source and the exposure detector (10), in respect of attenuation of radiation, and darkening of the image being detected by the image data receiving means (7) as a function of radiation incident on the image data receiving means, and further comprising means for determining the thickness of the object to be imaged (4) in the direction of a radiation beam emitted from said radiation source (1) when the object is positioned within the imaging area, an exposure detector (10) and means for determining the object density by comparing the signal to the modeled attenuation of radiation, and means for determining, on the basis of the aforesaid modelings, the determined object thickness, and the determined object density, at least one value of the at least one imaging parameter required to achieve a desired degree of darkening of the image and means for adjusting said at least one values accordingly.

16. Automatic exposure system according to claim 15, wherein a modeling of said at least one component (2, 3, 5, 6, 7, 8, 9) in respect of attenuation of radiation is stored on the aforesaid data storage means, said modeling uses an equation describing attenuation of coherent monochromatic radiation on the basis of a material composition and a thickness of the modeled component.

17. Automatic exposure system according to claim 15, wherein, for at least one of said modeled components (2, 3, 5, 6, 7, 8, 9), said data storage means stores the correlation between different radiation intensities and attenuation of radiation spectrum determined via empiric measurements.

18. Automatic exposure system according claim 15, wherein said image data receiving means (7) is a photographic film, and wherein the aforesaid data storage means contains a modeling of darkening of the image being detected by the image data receiving means, said modeling produced by taking into account the radiation quanta absorbed directly into the film (7) since having penetrated through a cover (6) of a film cassette and the quanta converted into light photons in an intensifying screen (8) and emitted from there to the film (7), on the basis of the modeled spectrum of the radiation obtained from the radiation source (1) and said modeling in respect of attenuation of radiation in at least one of the components (2, 3, 5, 6) of the imaging apparatus that lie between the radiation source (1) and the film (7), stored on said data storage means, wherein the at least one component includes the cover (6) of the film cassette.

19. Automatic exposure system according to claim 18, wherein the aforesaid storage means comprise means for determining the signal that should be obtained from the exposure detector (10) considering the radiation spectrum used for the imaging, the thickness of the object to be imaged (4) and the attenuation of the radiation according to the aforesaid modelings and assuming that the attenuation in the object to be imaged (4) is typical of the object and of average magnitude, means for determining the an exposure time according to said modelings and corresponding to said signal, and means for comparing the exposure detector signal measured during the exposure to the exposure detector signal determined on the basis of the modelings and adjusting the exposure time and/or some other imaging parameter to a value corresponding to the actual object density determined on the basis of said modelings, if the measured signal differs from the predetermined signal by more than a preset limit criterion.

20. Automatic exposure system according to claim 15, wherein for at least one known film type, the aforesaid data storage means contains a modeling of at least one imaging parameter leading to a desired darkening, said modeling being produced by using a correction factor representing deviation in darkening from the reciprocal law for the film type in question, and wherein the at least one imaging parameter is an exposure time.

21. Automatic exposure system according to claim 15, wherein the imaging apparatus is a mammography imaging apparatus, wherein the mammography imaging apparatus has at least one component (2, 3, 5, 6, 7, 8, 9) that lies between the radiation source (1) and the image data receiving means (7) and/or between the radiation source (1) and the exposure detector (10), and wherein the aforesaid data storage means contains a modeling of at least one of the following components: a radiation filter (2), compression plates (3, 5), a film cassette cover (6), a film (7), an intensifying screen(8), a film cassette bottom (8) and an exposure detector cover (9), modeled as a function of attenuation of radiation.

22. Automatic exposure system according to claim 15, wherein the aforesaid data storage means contains modelings of all components (2, 3, 5, 6) lying between the radiation source (1) and the image data receiving means (7), modeled as a function of attenuation of radiation.

23. Automatic exposure system according to claim 15, wherein the aforesaid data storage means contains modelings of all components (2, 3, 5, 6, 7, 8, 9) that lie between the radiation source and the exposure detector (10), modeled as a function of attenuation of radiation.

24. Automatic exposure system according to claim 15, wherein said system further comprises a plurality of exposure detectors (10).

25. Automatic exposure system according to claim 24, wherein said system further comprises means for measuring the signal of each detector (10) and for weighting these signals so that no part of the image produced will remain too light nor darken too much.

26. Automatic exposure system according to claim 24, wherein said at least one value of the at least one imaging parameter is a value corresponding to an exposure time, and further wherein said means for determining the at least one value includes means for evaluating said signals measured from the plurality of exposure detectors (10) on the basis of the magnitude of the measured signal and the density of the object (4), in order to determine whether the corresponding exposure detector (10) lies within the area under the object (4) or outside the area under the object (4), and further wherein any of said signals corresponding to an exposure detector (10) that lies outside the area under the object (4) are not taken into consideration by said means for determining said value corresponding to the exposure time.

27. Automatic exposure system according to claim 26, wherein said system further comprises means for determining a variation in the production of radiation quanta and providing compensation to compensate for said variations in the production of radiation of the radiation source, wherein said means for determining a variation basis the determination upon at least one of the signals measured from the plurality of exposure detectors (10) that corresponds to an exposure detector lying outside the area under the object (4).

* * * * *